(12) United States Patent
Jarnigan et al.

(10) Patent No.: US 6,455,268 B1
(45) Date of Patent: Sep. 24, 2002

(54) HYDROLYTIC ENZYME SUBSTRATES AND ASSAY METHOD

(75) Inventors: Kurt Jarnigan, San Mateo, CA (US); Roger Leger, Saint-Lambert (CA); Ving J. Lee; David Morgans, both of Los Altos, CA (US)

(73) Assignee: Iconix Pharmaceuticals Inc., Mountain View, CA (US)

( * ) Notice: Subject to any disclaimer, the term of this patent is extended or adjusted under 35 U.S.C. 154(b) by 2 days.

(21) Appl. No.: 09/706,342

(22) Filed: Nov. 3, 2000

Related U.S. Application Data (60) Provisional application No. 60/164,081, filed on Nov. 5, 1999.

(51) Int. Cl.[7] .............................. C12Q 1/34; C12Q 1/26; C12Q 1/00; G01N 33/53
(52) U.S. Cl. ............................. 435/18; 435/25; 435/4; 435/975
(58) Field of Search ................................ 435/18, 25, 4, 435/975

(56) References Cited

U.S. PATENT DOCUMENTS 5,208,148 A 5/1993 Haugland et al. ............. 435/18

FOREIGN PATENT DOCUMENTS

WO WO 96/30540 10/1996

OTHER PUBLICATIONS

Takakusa et al; Analytical Chemistry, vol. 73(5), p 939–942, 2001.*

Assfalg–Machleidt et al., "Membrane Permeable Fluorogenic Rhodamine Substrates for Selective Determination of Cathepsin L,"0 *Biol. Chem. Hoppe Seyler* 373(7):433–440 (1992).

Black et al., "Flow Cytometric Analysis of Xenobiotic Metabolism Activity in Isolated Rat Hepatocytes," *Cytometry* 14(3):334–338 (1993).

Burke et al., "Fluorescence–Microscopic Measurement of Intracellular Cytochrome P–450 Enzyme Activity (Ethoxyresorufin O–de–Ethylation) in Unfixed Liver Sections," *Biochem. J.* 212(1):15–24 (1983).

Ella et al., "A Flourescent Assay for Agonist–Activated Phospholipase D in Mammalian Cell Extracts," *Analytical Biochemistry* 218(1):136–142 (1994).

Fiering, S.N. et al., "Improved FACS–Gal: Flow Cytometric Analysis and Sorting of Viable Eurkaryotic Cells Expressing Reporter Gene Constructs," *Cytometry* 12(4):291–301 (1991).

Ganesh et al., "Flow Cytometric Determination of Aminopeptidase Activities in Viable Cells Using Fluorogenic Rhodamine 110 Substrates," *Cytometry* 20(4):334–340 (1995).

(List continued on next page.)

*Primary Examiner*—Louise N. Leary
(74) *Attorney, Agent, or Firm*—Robins & Pasternak LLP (57) ABSTRACT

Compounds of the invention have the structure D—L—A*, where L is a linking moiety that maintains D and A in a configuration compatible with FRET, D is a fluorescent donor moiety capable of causing an acceptor moiety to fluoresce by FRET, and A* is a fluorescent acceptor moiety capable of accepting energy from the donor moiety by FRET and fluorescing only after cleavage of one or more labile groups to provide acceptor A. These compounds are useful as fluorescent substrates for detection of enzymes in vivo.

17 Claims, 7 Drawing Sheets

OTHER PUBLICATIONS

Griffith et al., "Phosphatidylinostol Specific: Phospholipases C from *Bacillus cereus* and *Bacillus thuringiensis*," *Meth. Enzymol.* 197:493–502 (1991).

Gurtoo et al., "Cytochrome P–450 in a Cultured Human Lymphocyte Cell Line," *Biochemical Pharmacology* 27(22):2659–2662 (1978).

Klingel et al., "Flow Cytometric Determination of Cysteine and Serine Proteinase Activities in Living Cells with Rhodamine 110 Substrates," *Methods in Cell Biol.* 41:449–459 (1994).

Lorincz et al., "Enzyme–Generated Intracellular Fluorescence for Single–Cell Reporter Gene Analysis Utilizing *Escherichia Coli* β–Glucuronidase," *Cytometry* 24(4):321–329 (1996).

Lorincz et al., "Single Cell Analysis and Selection of Living Retrovirus Vector–corrected Mucopolysaccharidosis VIII Cells Using a Fluorescence–Activated Cell Sorting–based Assay for a Mammalian β–Glucuronidase Enzymatic Activity," *The Journal of Biological Chemistry* 274(2):657–665 (1999).

Meshulam et al., "Flow Cytometric Kinetic Measurements of Neutrophil Phospholipase A Activation," *The Journal of Biological Chemistry* 267(30):21465–21470 (1992).

Miller et al., "Flow Cytometric Techniques for Measurement of Cytochrome P–450 Activity in Viable Cells," *Methods in Cell Biology* 33:71–79 (1990).

Miller, A.J., "Ethylated Fluoresceins: Assay of Cytochrome P–450 Activity and Application to Measurements in Single Cells by Flow Cytometry," *Analytical Biochemistry* 133(1):46–57 (1983).

Nolan et al., "Fluorescence–Activated Cell Analysis and Sorting of Viable Mammalian Cells Based on β–D–Ga;actp-sodase Actovotu After Transduction of *Escherichia coli lacZ*," *Proc. Natl. Acad. Sci. U.S.A.* 85(8):2603–2607 (1988).

Rothe et al., "Flow Cytometric Analysis of Protease Activities in Vital Cells," *Biol. Chem. Hoppe Seyler* 373(7):547–545 (1992).

Stein et al., "Cloning and Expression of Human Arylsulfatase A," *The Journal of Biological Chemistry* 264(2):1252–1259 (1989).

Ubezio et al., "Flow Cytometric Detection of Hydrogen Peroxide Production Induced by Doxorubicin in Cancer Cells," *Free Radical Biology Medicine* 16(4):509–516 (1994).

Ulbricht et al., "Quantification of Intracellular Cathepsin Activities in Human Lung Tumor Cell Lines by Flow Cytometry," *Biol. Chem. Hoppe Seyler* 376(7):407–414 (1995).

Whitney et al., "A Genome–Wide Functional Assay of Signal Transduction in Living Mammalian Cells," *Nature Biotechnol.* 16(13):1329–1233 (1998).

Yancopoulos et al., "A Novel Fluorescence–Based System for Assaying and Separating Live Cells According to VDJ Recombinase Activity," *Molecular and Cellular Biology* 10(4):1697–1704 (1990).

Zlokarnik et al., "Quantitation of Transcription and Clonal Selection of Single Living Cells with β–Lactamase as Reporter," *Science* 279(5347):84–88 (1998).

* cited by examiner

HYDROLYTIC ENZYME SUBSTRATES AND ASSAY METHOD

This application claims benefit of Ser. No. 60/164,081 filed Nov. 5, 1999.

FIELD OF THE INVENTION

This invention relates generally to the fields of biochemistry and cellular biology. More particularly, the invention relates to compounds and methods for detecting and assaying enzyme activity in an intact cellular system.

BACKGROUND OF THE INVENTION

The detection of hydrolases and oxidases within living cells has been a difficult task. The primary problems associated with these assays are the difficulty in loading cells with the hydrolytic substrate under physiological conditions, leakage of the substrate and product out of the cells, and in the case of fluorescent substrates, high levels of background fluorescence caused by cellular components. Another factor that hinders in vivo determination of hydrolase activity is the pH optimum for fluorescence of the products as compared to the physiological pH. In the case of glycosidases (see e.g. Haugland et al., U.S. Pat. No. 5,208,148; S. N. Fiering et al., *Cytometry* (1991) 12(4):291–301; M. Lorincz et al., *Cytometry* (1996) 24(4):321–29; M. Lorincz et al., *J Biol Chem* (1999) 274(2):657–65; G. P. Nolan et al., *Proc Natl Acad Sci USA* (1988) 85(8):2603–07; G. D. Yancopoulos et al., *Mol Cell Biol* (1990) 10(4):1697–704), proteases (D. Irving, *Am Clin Lab* (1997) 16(10):16–17; S. Klingel et al., *Meth Cell Biol* (1994) 41:449–59; G. Rothe et al., *Biol Chem Hoppe Seyler* (1992) 373(7):547–54; B. Ulbricht et al., *Biol Chem Hoppe Seyler* (1995) 376(7):407–14; I. Assfalg-Machleidt et al., *Biol Chem Hoppe Seyler* (1992) 373(7):433–40; S. Ganesh et al., *Cytometry* (1995) 20(4):334–40), lipases or esterases, phospholipases A1 and A2 (A2 (T. Meshulam et al., *J Biol Chem* (1992) 267(30):21465–70), or dealkylases (A. D. Miller et al., *Meth Cell Biol* (1990) 33:71–79; K. A. Black et al., *Cytometry* (1993) 14(3):334–38; M. D. Burke et al., *Biochem J* (1983) 212(1):15–24; A. G. Miller, *Anal Biochem* (1983) 133(1):46–57; H. L. Gurtoo et al., *Biochem Pharmacol* (1978) 27(22):2659–62), or oxidases and peroxidases (P. Ubezio et al., *Free Radic Biol Med* (1994) 16(4):509–16), assays in living cells have been developed, but most suffer due to the issues outlined above. In the case of phosphatases (*Proc Natl Acad Sci USA* (1963) 50:1), phospholipases C and D (O. H. Griffith et al., *Meth Enzymol* (1991) 197:493–502; K. M. Ella et al., *Anal Biochem* (1994) 218(1):136– 42), or sulfatases (C. Stein et al., *J Biol Chem* (1989) 264(2):1252–59), assays in living cells have not been reported. An assay that overcomes some of the issues for beta-lactamase has been described (G. Zlokarnik et al., *Science* (1998) 279(5347):84–88; M. Whitney et al., *Nat Biotechnol* (1998) 16(13):1329–33; and Tsien et al., WO96/30540).

SUMMARY OF THE INVENTION

We have now invented compounds capable of detecting the activity of hydrolytic enzymes intracellularly, in intact cells. In general, the compounds comprise two moieties that are coupled together by a linker that spaces the moieties apart at a distance consistent with fluorescent resonance energy transfer (FRET). The first moiety is selected to be fluorescent, with an emission spectrum that overlaps the excitation spectrum of the second moiety, such that the first moiety is capable of acting as a resonance energy donor. The second moiety is selected to serve as a substrate for the enzyme to be examined, to exhibit fluorescence only after it has been acted upon by the enzyme, and to fluoresce by FRET when stimulated by resonance with the first moiety. The compounds of the invention are hydrophilic, and are retained within the cell after cleavage. The donor moiety fluorescence serves as an internal standard, while the ratio of acceptor moiety fluorescence to donor fluorescence indicates the percentage of compound hydrolyzed by the enzyme in question.

One aspect of the invention is a compound useful for detecting the activity of an enzyme in an intracellular environment, having the structure D—L—A*, where L is a linking molecule that maintains A and D at a distance suitable for FRET, D is a fluorescent donor moiety capable of fluorescing regardless of the presence or absence of the enzyme, and A* is a pre-fluorescent acceptor moiety capable of generating a signal by FRET only after modification to A by the target enzyme (for example, by cleaving a group that prevents fluorescence, or by adding a group that confers fluorescence).

One aspect of the invention is a compound of formula 1:

wherein $R_1$ is hydroxy, lower alkoxy, lower alkylamino, or di(lower alkyl)amino, $R_2$ is H or halo, $R_3$ and $R_4$ are each independently a sulfate, alkyl, acyl, acyloxymethyl, acyloxyethyl, amino acid, oligopeptide, polypeptide, nucleotide, oligonucleotide, polynucleotide, carbohydrate, polysaccharide, lipid, phospholipid, or a group hydrolysable by a phospholipase, $X_1$ is OH and $X_2$ is COOH, or $X_1$ and $X_2$ together form —COO—, $X_3$ is a linking group, and $X_4$ and $X_5$ are each independently —O—, —NH—, —LO—, or —LNH—, where L is a cleavable linker.

Another aspect of the invention is a method for measuring enzyme activity within a cell, comprising introducing a compound of the invention into a test cell, permitting an endogenous enzyme (if present) to cleave said substrate into first and second moieties, and measuring the fluorescence. Preferably, the ratio of fluorescence of said first moiety and said second moiety is measured.

Another aspect of the invention is a method of determining gene expression in a host cell, by inserting a polynucleotide encoding a selected enzyme so that it is operatively associated with a native regulatory sequence of said host cell, subjected the host cell to test conditions, contacting the host cell with a compound of the invention that is activated by said selected enzyme, and measuring the signal and/or the change in signal from said compound.

Another aspect of the invention is a method for selecting a compound of the invention for use with a selected enzyme, by providing a panel of host cells, wherein at least one of said host cells expresses a selected enzyme and at least one host cell does not express said enzyme, contacting the panel with at least one candidate compound, and selecting those compounds which provide a FRET signal in host cells which express the selected enzyme.

DETAILED DESCRIPTION

Definitions

The term "compound of the invention" refers to compounds having the structure D—L—A, or D—L—A*, where L is a linking moiety that maintains D and A in a configuration permissive for FRET, D is a fluorescent donor moiety capable of causing an acceptor moiety to fluoresce by FRET, and A* is an acceptor moiety capable of accepting energy from the donor moiety by FRET and fluorescing only after cleavage of one or more labile groups (thus providing A).

The term "donor" ("D") refers to a fluorescent moiety that is capable of emitting light at a frequency comparable to the absorbance frequency of an acceptor. Suitable donor moieties include coumarin, coumarin derivatives, and the like.

The term "acceptor" ("A") refers to a moiety that is capable of absorbing fluorescence resonance energy from a donor moiety, and fluorescing at a different frequency. Suitable acceptor moieties include, without limitation, fluorescein, rhodamine-110, fluorescein derivatives, rhodamine derivatives, and the like. The terms "protected acceptor", "acceptor*", "A*", and "pre-fluorescent" refer to acceptor moieties having one or more labile groups that disrupt the moiety's fluorescence, or that shift the absorbance and/or emission frequencies sufficiently that no signal is produced at the expected frequency. Pre-fluorescent moieties become fluorescent following removal of a labile functionality or protecting group, for example due to the enzymatic activity to be detected.

The term "labile group" or "labile functionality" refers to a moiety that can be removed from an acceptor moiety by enzymatic hydrolysis to render the acceptor moiety capable of FRET fluorescence. Suitable labile groups include, without limitation, amino acids, oligopeptides, polypeptides, nucleotides, oligonucleotides, farnesyl, prenyl and isoprenyl moieties, choline, carbohydrates and polysaccharides such as myo-inositol, 1-myo-inositol diphosphates, 1-mysinositol triphosphates, and 1-myo-inositol tetraphosphates, and the like, sulfates, $C_1$–$C_{20}$ alkyl or alkenyl, $C_1$–$C_{10}$ acyl, $C_1$–$C_4$ acyloxymethyl, $C_1$–$C_4$ acyloxyethyl, and the like. The particular labile group employed is determined by the enzyme to be detected, and is selected so that it can by removed by the enzyme. Preferably, the labile group is removed only by the enzyme under study. The labile groups can be identical or different.

The terms "linker" and "linking moiety" refer to a moiety that joins D and A (or A*), and maintains the fluorescent moieties in a configuration suitable for fluorescence of A by FRET. The linker preferably also includes one or more groups carrying a net charge or capable of forming hydrogen bonds, sufficient to increase the aqueous solubility of the compound of the invention. The term "cleavable linker" refers to an optional linker that joins one or more labile groups to a fluorophore, and that is rapidly and/or automatically removed following cleavage or loss of the labile group. A variety of cleavable linkers are known in the art. One form of cleavable linker comprises an electrophilic site and a nucleophilic site separated by a flexible spacer capable of forming a 5- or 6-membered ring, where one of the reactive sites is masked by the labile moiety to be cleaved. For example, a cleavable linker can have the form —CO ($CR_aR_b$)$_n$NH—, where n is 2, 3, or 4, and $R_a$ and $R_b$ are each independently H or alkyl, or other pendant groups that increase the likelihood of cyclization ($R_a$ and $R_b$ can also together form a ring): moieties of this form spontaneously cyclize and displace from the fluorophore after cleavage of the labile moiety. Alternatively, one can employ moieties that are rapidly cleaved by endogenous enzymes, as long as the linker cleavage is substantially inhibited by the presence of the labile group.

The term "alkyl" refers to a saturated straight, branched, or cyclic hydrocarbon moiety containing only carbon and hydrogen atoms, comprising from 1 to about 20 carbon atoms, for example, methyl, ethyl, propyl, prop-2-yl, n-butyl, but-2-yl, 2-methylprop-2-yl, hexyl, and the like. The term "lower alkyl" refers to alkyl moieties having from one to six carbon atoms. The term "alkenyl" refers to an alkyl moiety having at least one carbon-carbon double bond, such as, for example, prenyl, farnesyl, 4-hexenyl, and the like: "lower alkenyl" refers to an alkenyl moiety having from two to six carbon atoms. The term "alkynyl" refers to an alkyl moiety having at least one carbon-carbon triple bond, and may additionally have one or more double bonds. "Lower alkynyl" refers to an alkynyl moiety having two to six carbon atoms.

The term "halo" refers to fluoro-, chloro-, bromo-, and iodo-.

The terms "enzyme", "target enzyme", "enzyme of interest", "enzyme under study" and the like refer to the target of the method of the invention. The enzyme can be provided free in solution, attached or adsorbed to a solid support, expressed intracellularly, and the like. It is preferably expressed intracellularly, and can be native to the host cell or can be expressed heterologously.

The term "amino acid" as used herein refers to any of the 20 common amino acids found in polypeptides, for example, serine, alanine, glycine, tryptophan, aspartic acid, and the like. The term "polypeptide" refers to a polymer of amino acids joined by amide bonds, having at least two amino acids. The term "oligopeptide" refers to a polypeptide having at least two amino acids, and no more than about 20 amino acids. Polypeptides and oligopeptides can additionally comprise non-amino acid moieties, for example amino acid analogs or substitutes, reduced amide bonds, and the like, (either as part of the peptide backbone or bound to it as a side chain), carbohydrate moieties (for example, mimicking eukaryotic glycosylation of a protein), prenyl or other hydrocarbon moieties, lipids, and the like. Polypeptides and oligopeptides can be used discrete compounds of known sequence, or can have random sequences, or can be used as a mixture of a plurality of known and/or unknown sequences.

General Method

Compounds of the invention have the structure D—L—A, where L is a linking molecule that maintains D and A in a configuration compatible with FRET, D is a fluorescent donor moiety capable of fluorescing, and A is an acceptor moiety capable of fluorescing only after cleavage of one or more labile groups. As a general rule, the donor fluorophore will have an emission spectrum that overlaps the absorbance spectrum of the acceptor fluorophore. The acceptor must also be capable of fluorescing by FRET, and must have a structure capable of being derivatized with one or more labile groups that prevent FRET fluorescence while attached, but can be removed by an enzyme to be detected to restore fluorescence. It is preferred to use different fluorophores for the donor and acceptor, to facilitate distinguishing the FRET signal from the unreacted donor fluorescence, although this can be achieved by monitoring the change in fluorescence depolarization (L. W. Runnels et al., *Biophys J* (1995) 69:1569). Suitable donor-acceptor pairs include: fluorescein-tetramethylrhodamine; IAEDANS-fluorescein; EDANS-DABCYL; coumarin-fluorescein, and the like. Most of the readily accessible coumarin derivatives have maximum light absorbance at 390–425 nm, and maximum emission near 450–475 nm. Fluorescein derivatives absorb maximally at 470–495 nm, and emit near 515–535 nm, and thus are useful as acceptors when used with coumarin derivatives. The coumarin system is well suited for use in cytometry experiments because several of the less expensive lasers can excite well in the 350–425 nm region. Further, the fluorescein system is commonly used for many types of assay, and thus many different fluorimeters, fluorescent microscopes, cytometers and other detection systems optimized for use at those wavelengths are available. The donor and acceptor are joined by a linking group, which permits the donor and acceptor moieties to adopt a conformation capable of FRET, and further which insures that the molecule is sufficiently soluble in aqueous solution.

The linking group L can have a variety of different structures, as long as it maintains the acceptor and donor at a distance appropriate for FRET (about 10 to about 100Å), permits the acceptor and donor to adopt a conformation suitable for FRET, and preferably contributes to the aqueous solubility of the compound. The linking group ($X_3$) is presently preferred to have a length from about 8 to about 20 atoms long (counting only the atoms in the backbone chain), more preferably about 9 to about 14 atoms long, most preferably about 10 to about 12 atoms long. The linking group can have the structure $L_1$—$L_2$—$L_3$, where $L_1$ is —$(CH_2)_n$NH, —$(CH_2)_n$CO, or —(CHR)CO, where R is lower alkyl and n is 0 to 6; $L_3$ is CONH, COCH$_2$S, $(CH_2)_n R_{L3}$, CH$_2$CO, NHCO, CH$_2 R_{L3}$CH$_2$, O, S, NH(CS)NH, where $R_{L3}$ is N, O, or S; and $L_2$ is an aliphatic, alicyclic, or heterocyclic moiety, preferably bearing a carboxylic acid group. Preferred $L_2$ groups have one of the forms (type 1, 2, or 3) defined below. Type 1 $L_2$ groups have the general formula —$A_1$—N(D)B—, where $A_1$ (joined to $L_1$) is $(CH_2)_n$, $NH(CH_2)_{n=1}$, $S(CH2)_{n=1}$, or $O(CH2)_n$, where n is 0–4, B (joined to $L_3$) is $(CH_2)_m$, where m is 2–4, and D is $(CH_2)_m$COOH, $CH_2CH_2O(CH_2)_p$COOH where p is 1–4. Type 2 $L_2$ groups have the general formula —$A_2$—E—, where $A_2$ (joined to $L_1$) i $(CH_2)_n$, $NH(CH_2)_n$, $S(CH_2)_n$, or $O(CH_2)_n$, where n is 0–4, and E (joined directly to $L_3$) is C3–C7 alicyclic, phenyl or 6π heteroaryl (for example, furan, thiophene, oxazole, thiazole, thiadiazole, pyridyl), azaheterocyclics (for example azetidine, azetidinone, pyrrolidine, pyrrolidinone, piperidine, piperidinone, piperazine, oxazoline, thiazoline), oxaheterocyclics (for example, tetrahydrofuran, tetrahydropyran), any of which is substituted with at least one COOH, and can additionally be substituted with 1–4 groups selected from —$NO_2$, lower alkyl, and $CONH_2$. Type 3 $L_2$ groups have the general formula —$A_3$—$B_3$—CH($R_{L2}$)—, where $A_3$ (joined to $L_1$) is NH, O, or $CH_2$, $B_3$ is $CH_2$, CO, or CHOH, and $R_{L2}$ is H, $(CH_2)_n$, $R_x$, or $CH_2O(CH_2)_n R_x$, where n is 0–4 and $R_x$ is lower alkyl, lower cycloalkyl, COOH, $CONH_2$, phenyl, or phenyl substituted with 1–4 groups selected from halo, OH, $OCH_2COOH$, $NH_2$, and $CH_2NH_2$.

The labile groups ($R_3$ and $R_4$) are selected for their ability (a) to serve as a substrate for an enzyme to be detected, and (b) to inhibit FRET fluorescence by the acceptor moiety. The acceptor can bear one or more labile groups, which can be identical or different. Preferably, the labile groups serve as a specific substrate for the enzyme of interest. For example, where the enzyme in question is a glycosidase, the labile groups can be selected from the group (linked to the anomeric carbon): α- and β-D-glucose; α- and β-D-galactose; α- and β-D-glucuronic acid; α- and β-linked aldohexoses, α- and β-linked hexoses; aldopentoses; ketopentoses; 1-linked myo-inositol and its phosphorylated inositol phosphates; α- and β-1-fucose; α- and β-D-glucosamine; α- and β-D-galactosamine; α- and β-N-acetyl-D-glucosamine; α- and β-N-acetylmuramic acid; α- and β-N-acetylneuraminic acid; and α- and β-2-deoxy-D-ribose. Where the enzyme is a phospholipase D-type enzyme, the labile groups can be of the form —$PO_2OCH_2CH(OA_1)$—$CH_2OA_2$, where $A_1$ and $A_2$ are each independently selected from the group consisting of alkyl fatty acids of 2–22 carbon atoms, inclusive, and arachidonic, linolenic, linoleic, oleic, and palmitoleic acids. Where the enzyme has a phospholipase C-type activity, the labile groups are of the form —$CH_2CH(OA_1)CH_2OA_2$, where $A_1$ and $A_2$ are each fatty acids independently selected from the group consisting of alkyl of 2–22 carbon atoms, inclusive, and arachidonic, linolenic, linoleic, oleic, and palmitoleic acids. If the enzyme in question is a lipase, the labile groups can be moieties of the form —C(O)A, where A is selected from the group consisting of alkyl fatty acids of 2–22 carbon atoms, inclusive, and arachidonic, linolenic, linoleic, oleic, and palmitoleic acids. If the enzyme is a sulfatase, the labile group is preferably a sulfate. Enzymes having phosphatase activity can be detected using labile groups of the formula —$PO_2$—OR, where OR is hydroxy, serine, choline, myo-inositol, 1-myo-inositol diphosphates, 1-myo-inositol triphosphates, 1-myo-inositol tetraphosphates, or 1-myo-inositol phosphates with or without phosphates at other hydroxy sites. To detect enzymes having dealkylase activity (for example cytochromes such as cytochrome P450), one can use labile groups that are long chain alkyl moieties, having from 1 to 20 carbon atoms. Enzymes having oxidase or peroxidase activity can be detected using fluorescin (also known as dihydrofluroescein) as the acceptor moiety. To detect enzymes with protease or peptidase activity, rhodamine-110 (e.g., where $X_4$ and $X_5$ are each NH) can be the acceptor moiety. This system can be derivatized with some or all of the 20 common amino acids, and/or peptides of up to about 10 amino acids composed of any of the 20 common amino acids. The labile groups can be identical or different.

The compounds of the invention can further be derivatized by adding labile ester groups (for example, forming labile esters at existing carboxylate groups): such esters are generally cleaved upon entry into a cell under study by endogenous esterases. After such cleavage, the resulting charge on the compound at physiologic pH precludes the compound from leaving the cell. Derivatizing the compounds can enhance the rate of cell penetration. In general, phenol or amine moieties can be derivatized with lower acyl groups (for example, formyl, acetyl, n-butyryl, and the like), or lower alkoxycarbonyl groups. Carboxylic acid moieties can be derivatized with 1-(acyloxy)alkyl, acylthiomethyl, acyloxy-α-benzyl, δ-butyrolactonyl, methoxycarbonyloxymethyl, and the like, preferably acetoxymethyl.

The compounds are employed in the methods of the invention by incubating the compounds in a sample containing (or suspected of containing) the enzyme of interest, under conditions in which the enzyme is able to cleave the labile groups from the acceptor. The sample is illuminated with monochromatic light (for example, using a laser) at or near the absorption frequency of the donor fluorophore, and fluorescence measured at the donor frequency and the FRET acceptor frequency. The presence of FRET fluorescence indicates that an enzyme capable of removing the labile groups is present in the sample. One can measure the ratio of donor to FRET fluorescence as a function of time, and obtain the enzyme activity.

Compounds of the invention can be used in a variety of applications. In one method, the compounds are used to determine the activity of a known enzyme, either in vitro or in vivo (intracellularly). In another method, a plurality of compounds is prepared having a variety of different labile groups: the resulting library of compounds is then used to determine the activity of a target enzyme against different substrates (labile groups). This method is useful for defining the substrate specificity of the target enzyme, and studying its active site, as well as for optimizing the choice of labile group for studying the target enzyme. One can determine the activity of a plurality of enzymes against the library compounds to investigate compound specificity (e.g., the likelihood that a compound of the invention will be hydrolyzed by an enzyme other than the target enzyme), and also to identify similarities between different enzymes in terms of their ability to hydrolyze similar substrates.

Compounds of the invention can also be used to detect previously unknown enzymes, or the presence of known enzymes in previously unknown contexts. For example, a panel or library of compounds is prepared and tested against a large panel of enzymes having differing substrate specificities. Compounds that are not hydrolyzed by any of the enzymes are then administered to cells, which are observed for the appearance of FRET fluorescence. Appearance of a FRET signal indicates the presence of an enzyme capable of hydrolyzing the labile groups, and thus tentatively indicates the presence of a new enzyme. If a FRET signal is not observed, the test cell can be further subjected to a variety of stimuli and varying environmental conditions (e.g., changes in temperature, pressure, pH, ionic strength, contact, adhesion, nutrient concentration, mechanical strain, deformation, cytokine concentration, and the like) to determine whether the cell is capable of expressing a target enzyme under altered conditions. Enzymes that form a part of an alternate metabolic pathway (for example, a salvage pathway) can be discovered by performing such experiments in a variety of deletion mutants.

In another method, the compounds of the invention are useful for identifying enzymes that are expressed only rarely, or under specific conditions. For example, one can administer a compound of the invention to test cells that are unable to hydrolyze the compound under normal conditions. The cell is then subjected to a variety of different environmental conditions or stimuli, and examined for the appearance of FRET fluorescence, indicating the expression of an enzyme capable of hydrolyzing the labile groups. In cases in which the cells is capable of hydrolyzing the selected compound, it is possible to suppress expression of the responsible enzyme, for example by making a deletion mutant or by administering an antisense molecule, and thus detect other enzymes having the same substrate specificity (or an overlapping specificity) as a known enzyme.

In another method, the compounds of the invention are useful for studying alterations in target enzyme activity as a function of other factors. For example, a host cell capable of expressing the target enzyme is selected or produced (for example, by transformation or transfection with a polynucleotide encoding the target enzyme, or infection with a virus encoding the enzyme). The host cell is then subjected to the test condition (for example, contact with a drug candidate, heterologous protein, heterologous gene, or the like), and the compound of the invention administered at a variety of time points later (either to the same cell, or to different replicates). The enzyme activity is determined from the FRET fluorescence at each time point, and used to determine if the enzyme activity is affected by the test conditions.

Compounds of the invention can be formulated with a suitable carrier, in a variety of liquid or solid formats, for ease of addition to cell cultures (or host cells in other formats), or for administration to a test subject, for example by injection. As used herein, a "suitable carrier" is a diluent that is capable of dissolving, suspending, or absorbing the compound of the invention, is not unacceptably cytotoxic, and does not cause experimental interference (for example, fluorescent quenching). Formulations can be designed for use at the concentration as packaged, or can be packaged as a concentrate for dilution prior to use. Suitable liquid carriers can be aqueous in whole or part, and will generally exclude components that are toxic to the cells to which the compound will be administered. Exemplary liquid carriers include, without limitation, dimethylsulfoxide (DMSO), DMF, aqueous solutions of DMSO and/or DMF, liposomal suspensions, $CH_2Cl_2$, phosphate buffered saline (PBS), Ringer's solution, distilled water, and the like. Carriers, whether liquid or solid, can include components such as antibiotics, preservatives, antioxidants, buffering agents, and the like. Solid formulations can further include components such as bulking agents, cryoprotectants, dispersing agents, and the like. However, it is preferred to avoid the use of components that can interfere with experimental conditions. In solid formulations, the compound can take the form of, for example, an amorphous solid, a lyophilized powder, a crystalline solid or powder, or a liquid adsorbed on a solid carrier.

Formulations, whether liquid or solid, can be packaged in bulk form, or in "unit dose" form designed to contain an amount of compound suitable for one or a predetermined number of experiments. Packaged formulations typically further comprise a printed description of the contents and/or one or more methods for using the contents.

EXAMPLES

The following examples are provided as a guide for the practitioner of ordinary skill in the art. Nothing in the examples is intended to limit the claimed invention. Unless otherwise specified, all reagents are used in accordance with the manufacturer's recommendations, and all reactions are performed at standard temperature and pressure.

Example 1

(Synthesis)

(A) Following the procedure described in Tsien, WO96/30540, the compound 5-chloro-2,4-dihydroxybenzaldehyde is prepared. Piperidine is added to a solution of 5-chloro-2, 4-dihydroxybenzaldehyde and dimethyl malonate in methanol, and the reaction mixture heated at reflux overnight. The mixture is cooled and concentrated to about ¼ the original volume, then filtered and air-dried to provide the intermediate 6-chloro-7-hydroxycoumarin methyl ester (the "donor" component).

(B) 4-(N-Boc-amino)butylamine and 6-chloro-7-hydroxycoumarin methyl ester are mixed in MeOH and heated at reflux for 1 hour. The reaction mixture is cooled, and the solid filtered and air dried to provide the intermediate N-(4-aminobutyl)-5-chloro-6-hydroxycoumarinamide ($^1$H nmr, 300 MHz, $d_6$—DMSO: δ1.57 (m, 4H), 2.78 (m, 2H), 3.29 (m, 5H, $CH_2N$, includes OH and $NH_2$), 5.98 (s, 1H), 7.54 (s, 1H), 8.33 (s, 1H), 8.66 (t, J=6.0, 1H, NH). MS (ES+) 311.4 (M+H)).

(C) Hydroxybenzotriazole monohydrate ("HOBT") and ethyl-dimethylaminopropylcarbodiimide are added to a solution of Fmoc-Glu(O-tBu)-OH in DMF and stirred at 0° C. under a nitrogen atmosphere for 1 h. N-(4-aminobutyl)-5-chloro-6-hydroxycoumarinamide is added, and the mixture stirred for 1 h. Water is added, and the resulting solid is separated by centrifuge (15 min at 6000 rpm, 4° C.). A second aliquot of water is added, and the solid centrifuged again. The resulting product is vacuum dried, dissolved in chloroform, filtered through a nylon pad and concentrated to provide N-(4-(2-(Fmoc-amino)-4-carboxybutyramide)-1,4-diaminobutyl) -6-chloro-7-hydroxycoumarinamide t-butyl ester (1C).

1C (D) The HOBT ester is prepared as described in part (C) above, followed by addition of N-(4-aminobutyl)-5-chloro-6-hydroxycoumarinamide. The resulting compound is condensed with 5-(carboxamido)fluorescein diacetate (5-CFDA, Calbiochem), and purified in the same manner to provide 4-(5-chloro-6-hydroxycoumarinamido)butyl-5-carboxamidofluorescein diacetate. $^1$H nmr (300 MHz, $CDCl_3$):δ1.79 (m, 4H), 2.31 (s, 6H), 3.54 (m, 2H), 3.68 (m, 2H), 5.92 (s, 1H), 6.81 (m, 4H), 7.12 (m, 2H), 7.29 (d, J=7.5, 1H), 7.93 (s, 1H), 8.10 (t, J=5.4, 1H, NH), 8.39 (dd, J=8.1, 1.5, 1H), 8.89 (s, 1H), 9.04 (t, J=6.0, 1H, NH), 9.19 (s, 1H). MS (ES–) 751.4 (M–H).

(E) Intermediates useful for providing the "acceptor" portion of compounds of the invention can be prepared from fluorescein derivatives. For example, 2-aminofluorescein is protected with $Boc_2O$, and reacted with O,O,O-triacetyl-1-bromo-methylglucuronate and $Ag_2O$ to derivatize both phenolic hydroxyl groups. This intermediate is treated with trifluoroacetic acid (TFA) followed by CDI to provide intermediate 1E:

1E

Intermediates of this form are useful for preparing compounds of the invention for use in detection of glycolytic enzymes. Compounds useful for detecting the activity of other enzymes are similarly prepared, substituting the appropriate enzyme substrate for the carbohydrates.

(F) Acceptor and Donor intermediates can be coupled by any convenient reaction. For example, intermediates 1C and 1E above can be coupled by treating 1C with piperidine in DMF, adding 1E, hydrolyzing with TFA, and treating with DEA, $H_2O$, and methanol to form a compound of the invention ("1F", also called "7CG-FDG"):

1F

Example 2

(Synthesis)

(A) A solution of di-t-butyldicarboxylate (7.2 g), fluorsceinamine (1.15 g) and methanol (20 ml) was stirred at ambient temperature for 30 h. the methanol is removed in vacuo and the residue titurated with $CH_2Cl_2$ (50 ml) to provide an orange solid. The orange solid is filtered and air-dried to provide N-Boc-fluoresceinamine isomer I (1.40 g, 90%). $^1$H NMR (300 MHz, DMSO-$d_6$) δ1.53 (s, 9H), 6.55 (m, 4H), 6.64 (m, 2H), 7.14 (d, J 9.0 Hz, 1H), 7.73 (dd, J 8.7, 1.5 Hz, 1H), 8.08 (s, 1H), 9.86 (s, 1H, NH), 10.07 (broad s, 2H, OH). Mass spec. (ES–) 446.4.

(B) N-Boc-5-aminofluorescein di-β-glucoronic acid hexaacetate dimethyl ester. This compound was prepared in a manner similar to the procedure described by Haugland et al., U.S. Pat. No. 5,208,148. To a well-stirred suspension of N-Boc-fluoresceinamine isomer I (as prepared in part A above) (229 mg) and pulverized 4 Å molecular sieves (1.5 g) in acetonitrile (3 ml), is added silver carbonate (0.46 g) and acetobromoglucoronic acid dimethyl ester (0.6 g). After the reaction mixture is stirred 15 h, another portion of silver carbonate (0.46 g) and acetobromoglucoronic acid dimethyl ester (0.6 g) is added and the solution is stirred 22 h. A third and final portion of silver carbonate (0.46 g) and acetobromoglucoronic acid dimethyl ester (0.6 g) is added and the solution is stirred 22 h. The reaction mixture is filtered through a nylon pad (0.45 μm) and the mother liquor is concentrated. The residue is purified by flash column chromatography (5% $CH_3CN/CH_2Cl_2$), followed by preparative thin layer chromatography (15% $CH_3CN/CH_2Cl_2$) to give the title compound (110 mg, 20%) as an off white solid. $^1$H NMR (300 MHz, $CDCl_3$) δ1.54 (s, 9H), 2.05 (s, 18H), 3.72 (s, 3H), 3.74 (s, 3H), 4.24 (m, 2H), 5.19 (t, J 6.8 Hz, 2H), 5.24–5.37 (m, 6H), 6.66–6.75 (m, 4H), 6.86 (s, 1H, NH), 6.78 (dd, J 2.4, 2.4 Hz, 2H), 6.98 (d, J 8.1 Hz, 1H), 7.71 (dd, J 8.1, 1.8 Hz, 1H), 7.96 (d, J 1.8 Hz, 1H). Mass Spec (ES+) 1080.4.

(C) Succinic acid derivative. A solution of N-Boc-5-aminofluorescein di-β-glucoronic acid hexaacetate dimethyl ester (61 mg) in $CH_2Cl_2$ (1 ml), at 0° C., is added TFA (1 ml) and anisole (200 μl). The reaction mixture is stirred 30 min. at 0° C., then 30 min at ambient temperature. The mixture is poured into chloroform, washed twice with saturated sodium bicarbonate and once with brine, dried over $Na_2SO_4$ and concentrated. Mass spec (ES+) 980.4. The residue is dissolved in dimethylformamide (DMF, 1 ml) and treated with succinic anhydride (56 mg). The reaction mixture is stirred 16 h and treated again with succinic anhydride (60 mg) and stirred 15 h. The solution is concentrated to dryness under vacuum (0.5 mmHg) and the residue is purified by flash column chromatography (0→1→5→10% MeOH/ $CH_2Cl_2$). The resulting material is triturated with ether and filtered to give the succinate derivative as a slightly yellow solid (36 mg, 59%). $^1$H NMR (300 MHz, DMSO-$d_6$) δ2.01 (broad s, 20H), 2.58 (m, 2H), 3.75 (d, 2H), 5.13 (m, 4H), 5.44 (m, 2H), 5.80 (d, 2H), 6.79 (m, 4H), 7.05 (broad s, 2H), 7.24 (d, 1H), 7.79 (d, 1H), 8.36 (s, 1H), 10.43 (s, 1H, NH), 12.18 (broad s, 1H, $CO_2H$). Mass spec (ES-) 1078.4.

(D) To a solution of Fmoc-Glu(O-t-Bu)-OH (56 mg) in DMF (1.1 ml), is added HOBT (22 mg) and ethyldimethylaminopropylcarbodiimide (42 mg) at 0° C. under a nitrogen atmosphere. The mixture is stirred at that temperature for 1 h. N-(4-aminobutyl)-5-chloro-6-hydroxycoumarin (34 mg) is then added, and the reaction mixture is stirred at 0° C. for another hour. Water (1 ml) is then added, and the resulting solid is separated by centrifuge (6000 rpm, 15 min at 4° C.). Another portion of water (1 ml) is added and the centrifugation is repeated. The resulting solid is vacuum dried, dissolved in chloroform, filtered through a nylon pad and concentrated to give N-(4-(2-Fmoc-amino-4-carboxybutyramide)-1,4-diaminobutyl)-6-chloro-7-hydroxycoumarinamide tert-butyl ester (99 mg) as a solid.

(E) (4-(2-Fmoc-amino-4-carboxybutyramide)-1,4-diaminobutyl)-6-chloro-7-hydroxycoumarinamide t-butyl ester. A solution of 20% diethylamine in $CH_3CN$ (2 ml) is added to N-(4-(2-Fmoc-amino-4-carboxybutyramide)-1,4-diaminobutyl)-6-chloro-7-hydroxycoumarinamide t-butyl ester (99 mg) and stirred for 40 min. at ambient temperature. The reaction mixture is then concentrated and the residue triturated with ether (1 ml). The solid is then treated with hot $CH_3CN$ and allowed to cool in an ice bath. The resulting solid is filtered and rinsed once with ether and dried to give the title compound (24 mg, 43%) as a slightly yellow solid. $^1$H NMR (300 MHz, DMSO-$d_6$) δ1.40 (s, 9H), 1.48 (m, 4H), 1.83 (m, 2H), 2.26 (m, 2H), 3.09 (m, 2H), 3.50 (m, 3H), 6.04 (s, 1H), 7.58 (s, 1H), 8.22 (m, 1H, NH), 8.37 (s, 1H), 8.6 (m, 1H, NH). Mass spec. (ES+) 494.5.

(F) Coupling of the succinate derivative (C) with (E). To a solution of (C) (5.3 mg) in DMF (0.1 ml) at 0° C. is added HOBT (2 mg) and ethyl-dimethylaminopropylcarbodiimide (4 mg), and the solution stirred at 0° for 1 h. A solution of the compound prepared in part (E) above (3 mg) in DMF (0.1 ml) is then added and the reaction mixture is allowed to stir 1 h. at 0° C. then 1 h. at ambient temperature. The mixture is cooled back down to 0° and 1,5 ml of ice cold water is added and the whole is stirred for 10 min. The solid is filtered and air dried. This material contains impurities but is used anyway as such in the next step. $^1$H NMR (300 MHz, DMSO-$d_6$) δ1.38 (s, 9H), 1.42 (m, 6H), 2.00 (s, 18H), 2.19 (m, 4H), 2.60 (m, 2H), 3.06 (m, 4H), 3.62 (s, 6H), 4.08 (m, 1H), 4.74 (d, J 9.9, 2H), 5.07 (m, 4H), 5.41 (m, 2H), 5.79 (m, 2H), 6.72–6.94 (m, 6H), 7.03 (m, 2H), 7.12 (d, J 8.1, 1H), 7.79 (d, J 7.5, 1H), 7.82 (m, 1H), 8.01 (s, 1H), 8.07 (d, J 7.5, 1H), 8.37 (s, 1H), 8.58 (m, 1H), 8.71 (s, 1H). Aromatic region contains NH's. Mass spec. (ES-) 1556.8.

(F)

(G) Deprotection of compound (F). To a solution of the compound prepared in part (F) above (2 mg) in $CH_2Cl_2$ (200 μl) at 0° C. is added TFA (200 μl), and the solution stirred at 0° C. for 1 h and at ambient temperature for 2.5 h. The reaction mixture is cooled to 0° C. and the solvent removed with a stream of $N_2$ followed by vacuum. The residue (mass spec (ES-) 1275.5) is then dissolved in $NEt_3$ (200 μl) and MeOH (100 μl). Water is slowly added to keep the temperature at 20° C. The reaction mixture is stirred at ambient temperature for 18 h. The solvent is removed by a stream of nitrogen, and the residue is purified by reverse phase chromatography. Using a Phenomenex Ultremex 5 C8 reverse phase column (310×10 mm) with a 10% $CH_3CN$/($NH_4OAc$ 10 mM) to 50% gradient, a flow rate of 2.5 ml/min and detection at 254 nm. (Gradient: 0 to 2 min 10% $CH_3CN$/ ($NH_4OAc$ 10 mM); 2 to 20 min 10 to 50% gradient; 22 to 32 min 50%. The desired compound, having a retention time of 10.8 min., was collected and lyophilized to give a yellow solid. Mass spec. (ES+) 1221.3

(H) Similarly, proceeding as described above but with appropriate substitution of starting materials, the following compounds were prepared:

"J"

"K"

"L"

"M"

Example 3

(In vitro Demonstration)

Ninety-six well microtiter plates were prepared containing duplicate samples, each sample containing 4-(5-chloro-6-hydroxycoumarinamido)butyl-5-carboxamidofluorescein diacetate ("Compound 11", 2 mM, 2 µL) in DMSO with phosphate buffered saline (PBS, 200 µL, pH 7.0). To each well was added orange peel acetylesterase (OPAE, Sigma, St. Louis, Mo., 5 µL, 39 U/mL) as a suspension in $(NH_4)_2SO_4$ (2.5 M) and sodium oxalate (0.1 M). A set of control samples was prepared in which the OPAE was replaced with PBS (no enzyme). The mixtures thus had a final concentration of 19 µL Compound, 0.97% DMSO, 60 mM $(NH_4)_2SO_4$, 2.4 mM sodium oxalate, and 0.94 U/mL OPAE. The plate was read prior to OPAE addition, at time 0, and at 5, 10, 30, 60, and 150 minutes after addition. Each reading was taken at three wavelength pairs using a Molecular Devices fmax fluorescent plate reader: excite 485/emission 530 (to measure fluorescein fluorescence); excite 350/emission 530 (to measure FRET fluorescence); and excite 530/emission 460 (to measure coumarin fluorescence).

Figure 1:
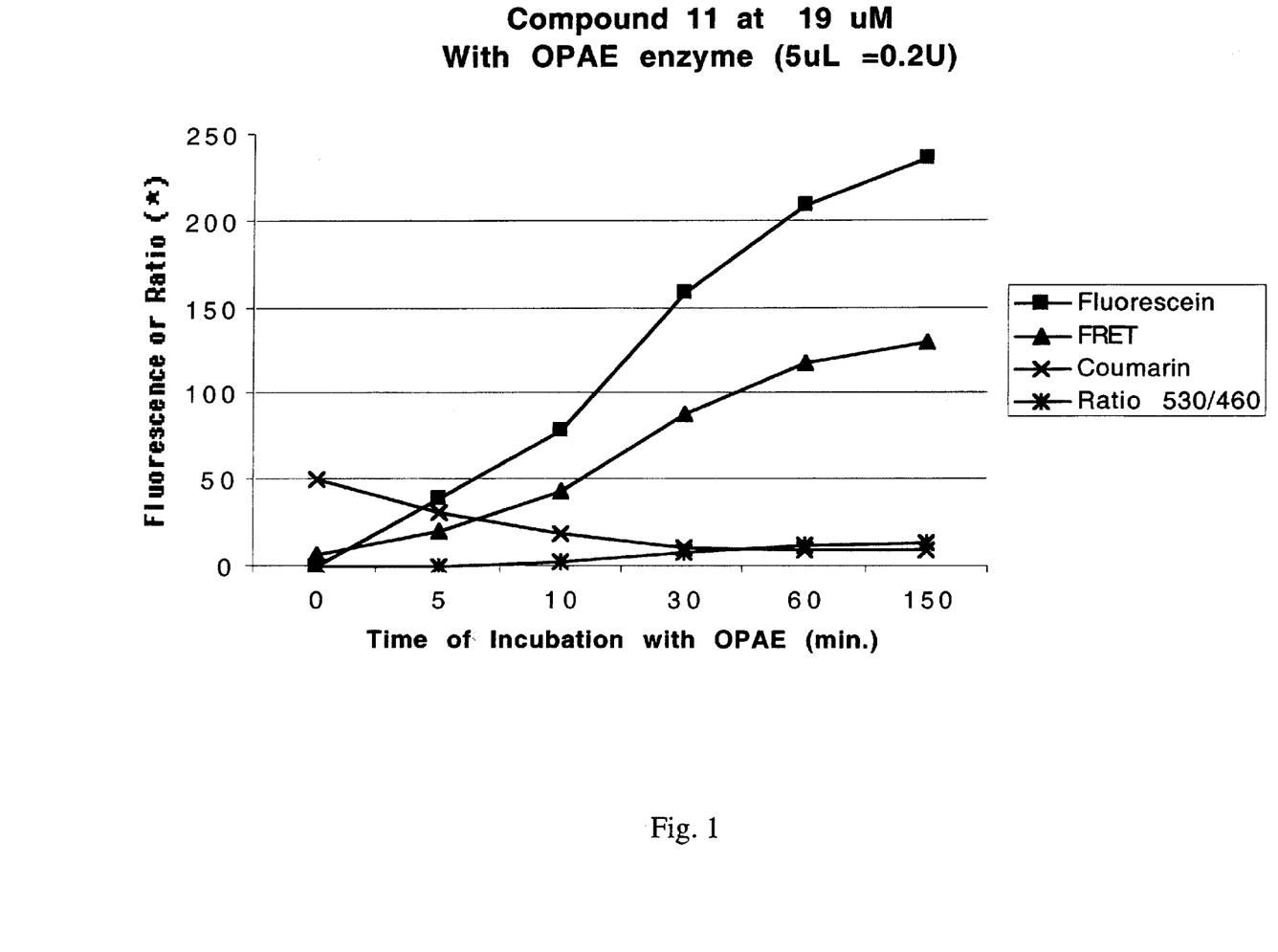
FIG. 1 is a graph showing the change in fluorescence of a compound of the invention (compound 11) during in vitro hydrolysis with orange peel acetylesterase (OPAE). This figure compares excitation at 485 nm/emission at 530 nm (squares) (normal fluorescein fluorescence), excitation at 350 nm/emission at 460 nm (×) (normal coumarin fluorescence), excitation at 350 nm/emission at 530 nm (triangles) (FRET fluorescence), and the ratio of emission at 530 nm to emission at 460 nm with excitation at 350 nm (ratio of FRET to fluorescein fluorescence).
Figure 2:
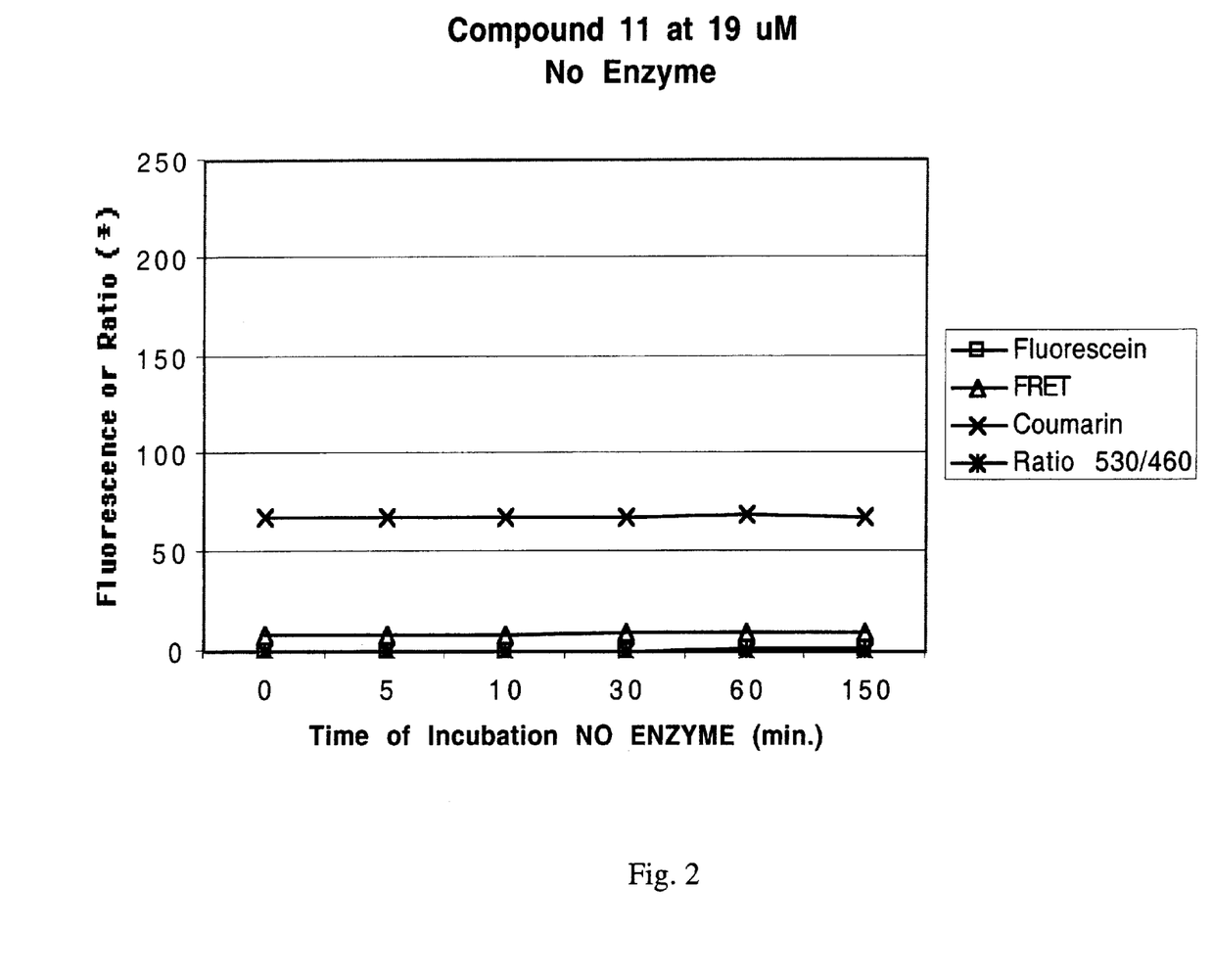
FIG. 2 is a graph showing the lack of change in fluorescence of compound 11 in the absence of OPAE.
Figure 3:
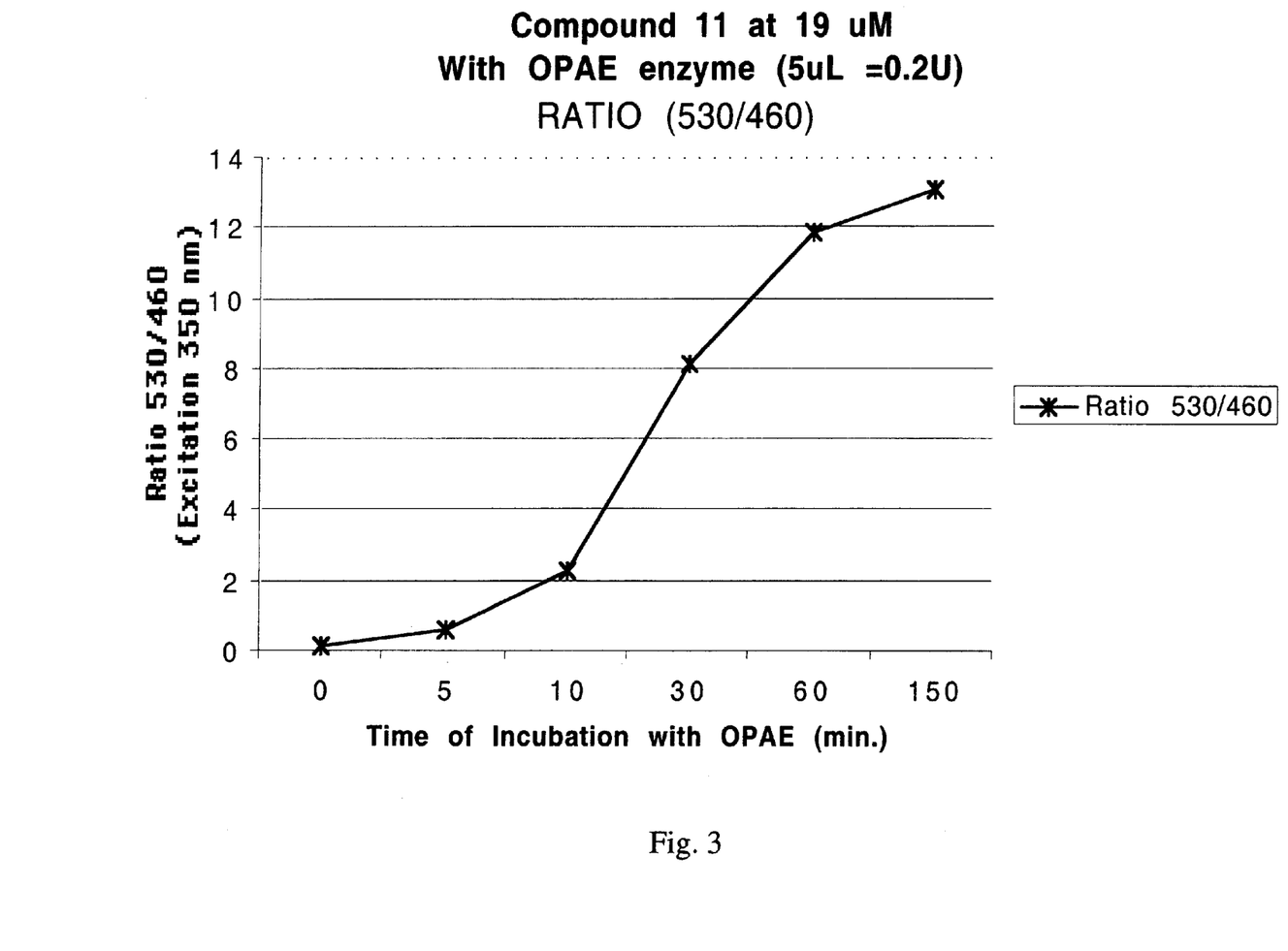
FIG. 3 is a graph showing the 530 nm/460 nm emission ratio depicted in FIG. 1 at an expanded scale.

FIG. 1 shows the change in fluorescence of Compound 11 as a function of time due to hydrolysis by OPAE, and very low rates of non-enzymatic hydrolysis. The decrease in fluorescence of the coumarin moiety in the presence of OPAE demonstrates quenching of donor fluorescence, a characteristic indication that FRET is occurring. Thus the linker used for Compound provides the necessary length and flexibility to allow FRET to occur. These results also indicate that fluorescein ethers and esters of the types disclosed herein can be enzymatically cleaved to reveal the fluorescence of the fluorescein system, while the non-enzymatic rate of hydrolysis is low. The large change in 530 emission to 460 emission ratio is that expected for a system in which FRET may occur. FIG. 2 shows that the compound fluorescence does not change in the absence of enzyme. FIG. 3 shows the ratio of FRET fluorescence to fluorescein fluorescence at an expanded scale.

A control set of experiments was preformed as above, but substituting a mixture of equal molar amounts of 5-carboxyfluorescein diacetate (5-CFDA, Calbiochem) and 6-chloro-7-hydroxycoumarin methyl ester. This mixture was non-fluorescent at 530 nm prior to OPAE addition and was fluorescent at 460 nm. After addition of OPAE, the fluorescein fluorescence at 530 nm increased rapidly, indicating OPAE-mediated hydrolysis of the 5-carboxyfluorescein diacetate. However, in this mixture of unlinked coumarin and fluorescein moieties, the fluorescence of the coumarin diminish only slightly (not shown). Furthermore, in this unlinked mixture case, the ratio of 530 nm to 460 nm only changed from 0.13 to 0.7; in contrast to the ratio change for the compound above, from 0.13 to 13.5. These controls indicate that FRET does not occur between noncovalently linked fluorescein and coumarin motities, but occurs readily when these moieties are linked.

Example 4

(In vitro Demonstration)

Figure 4:
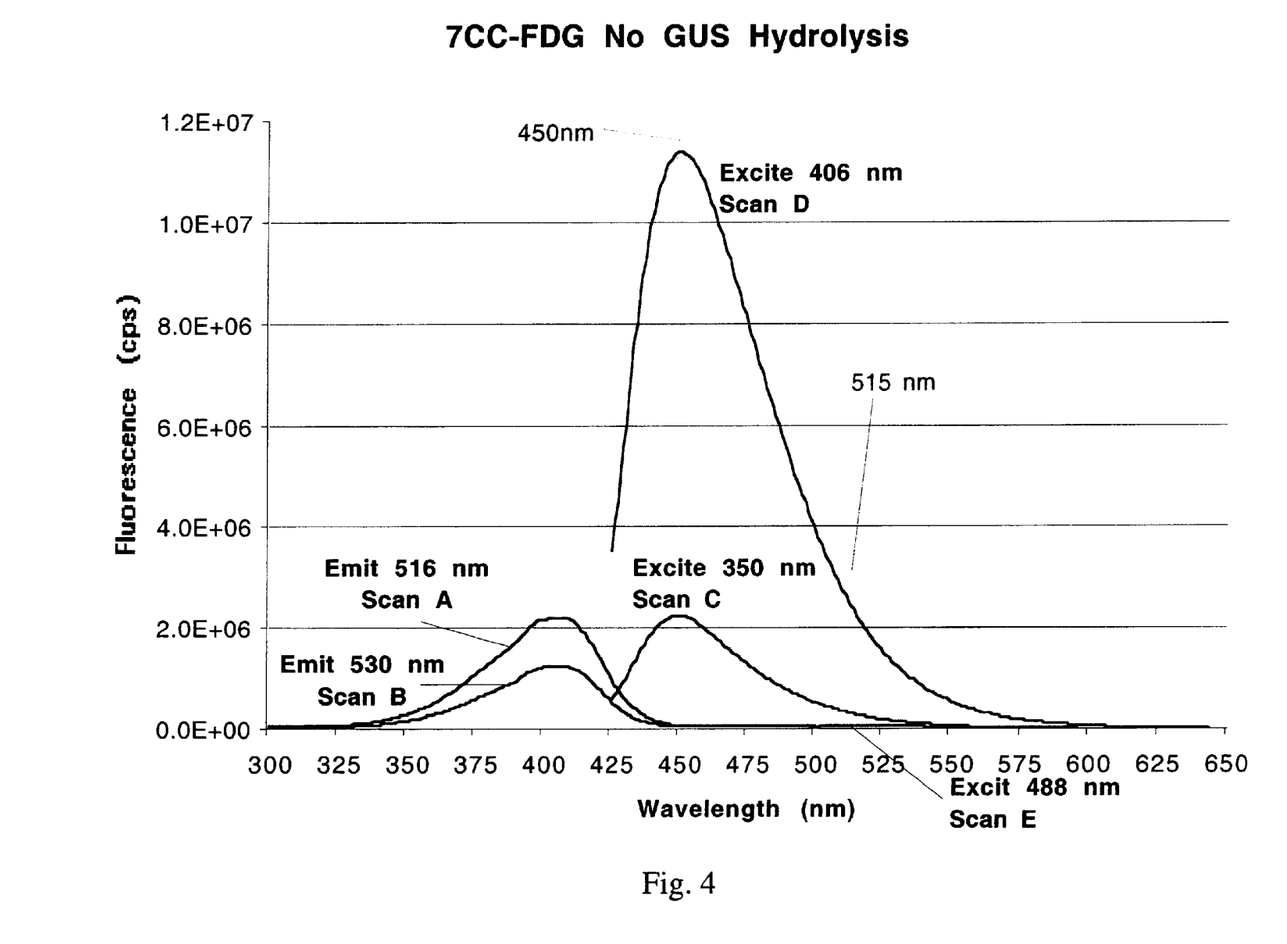
FIG. 4 is a graph showing the fluorescence excitation and emission spectra of a compound of the invention (without hydrolysis) as a function of wavelength when excited at 350–500 nm with emission measured at 516 nm (Scan A) or 530 nm (Scan B), or excited at 350 nm (Scan C) or 406 nm (Scan D) with emission measured at 425–650 nm, and when excited at 488 nm with emission measured at 500–650 nm (Scan E).
Figure 5:
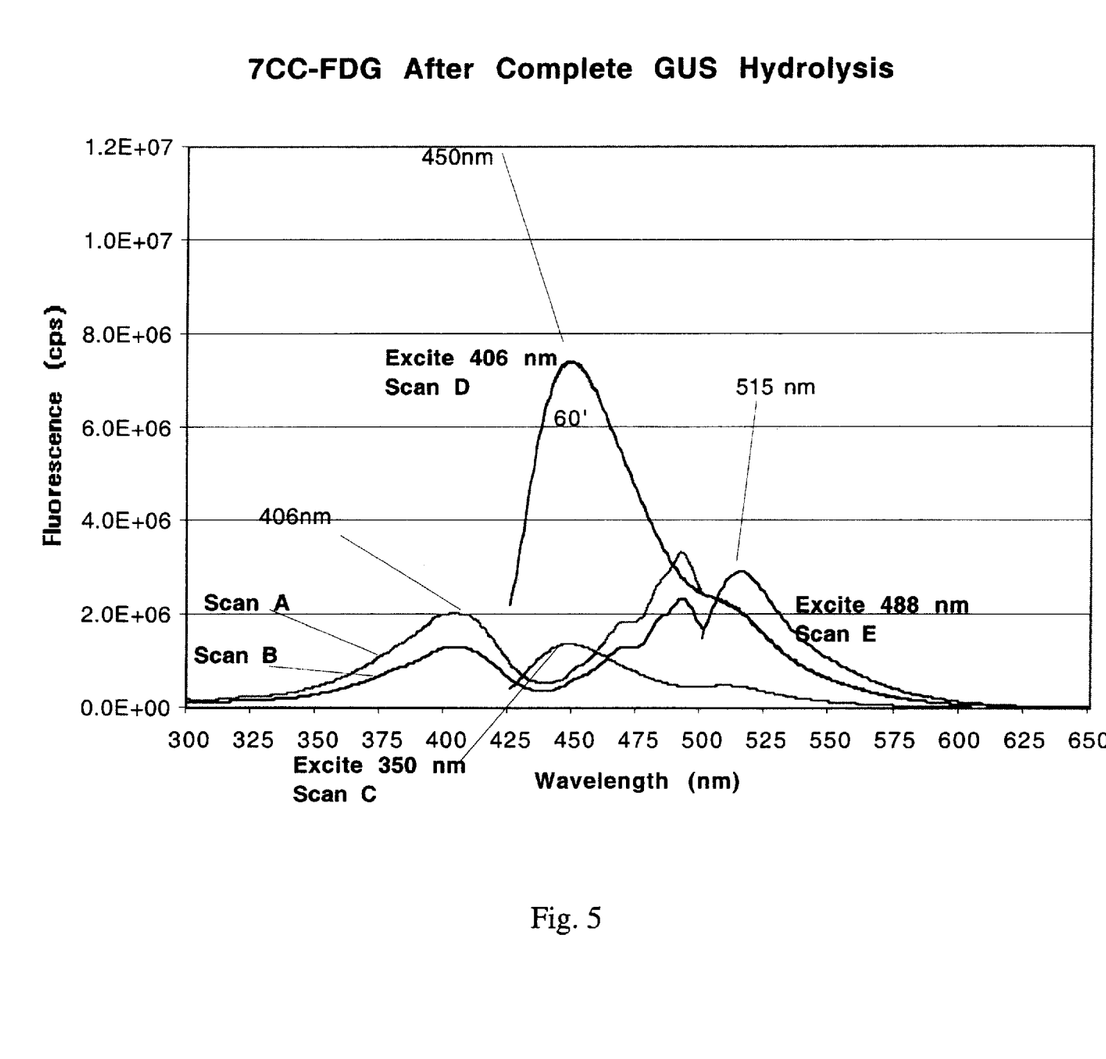
FIG. 5 is a graph showing the fluorescence as a function of wavelength of the same compound examined in FIG. 4 after hydrolysis with β-glucuronidase (GUS) for 60 minutes, with excitation and emission recorded at the same frequencies as described in FIG. 4.
Figure 6:
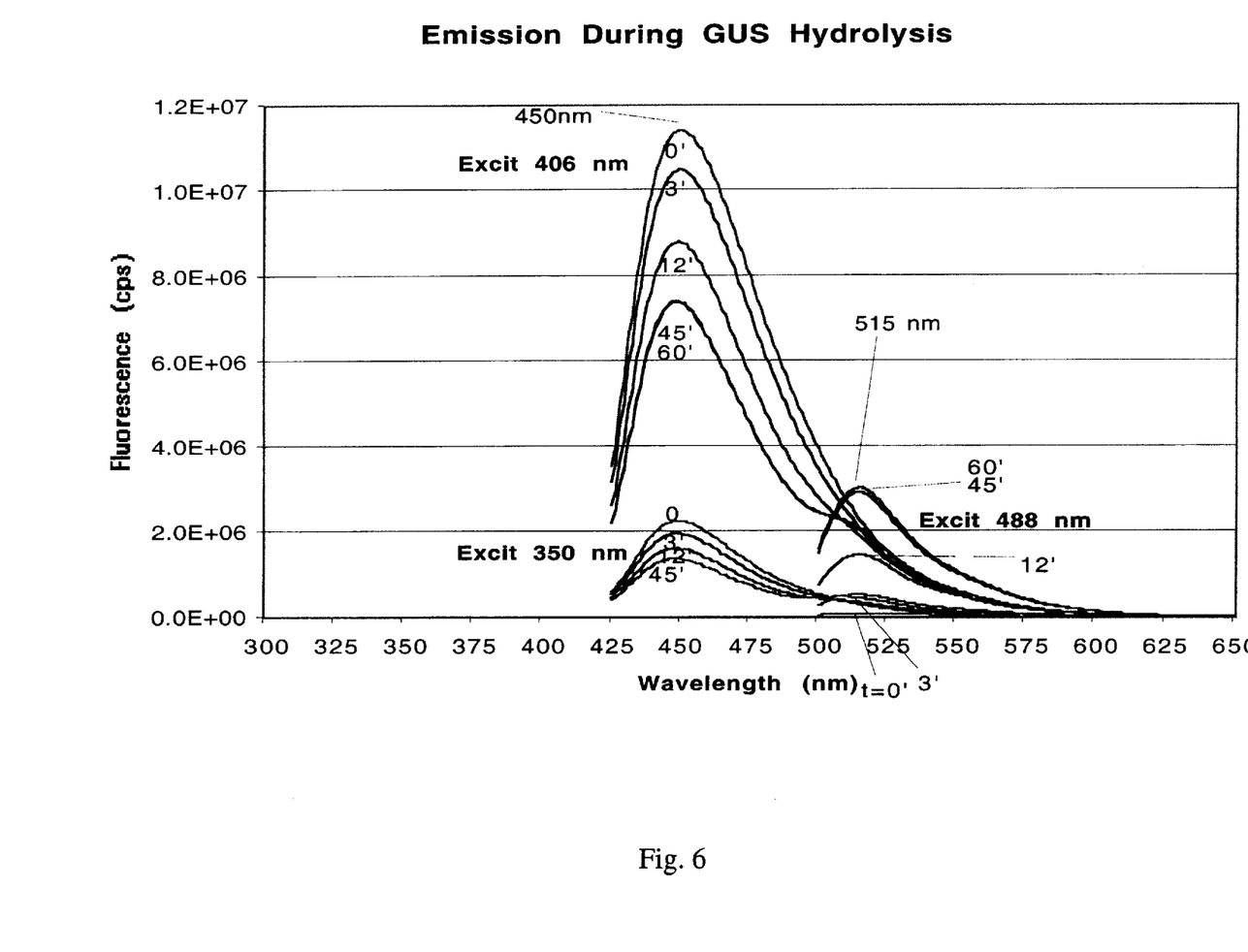
FIG. 6 is a graph showing the fluorescence emission of the same compound examined in FIG. 4 during hydrolysis with β-glucuronidase (GUS) at 0, 3, 12, 45, and 60 minutes as a function of wavelength, with excitation at 350 nm, 406 nm, and 488 nm (Scan C, Scan D, and Scan E, respectively).
Figure 7:
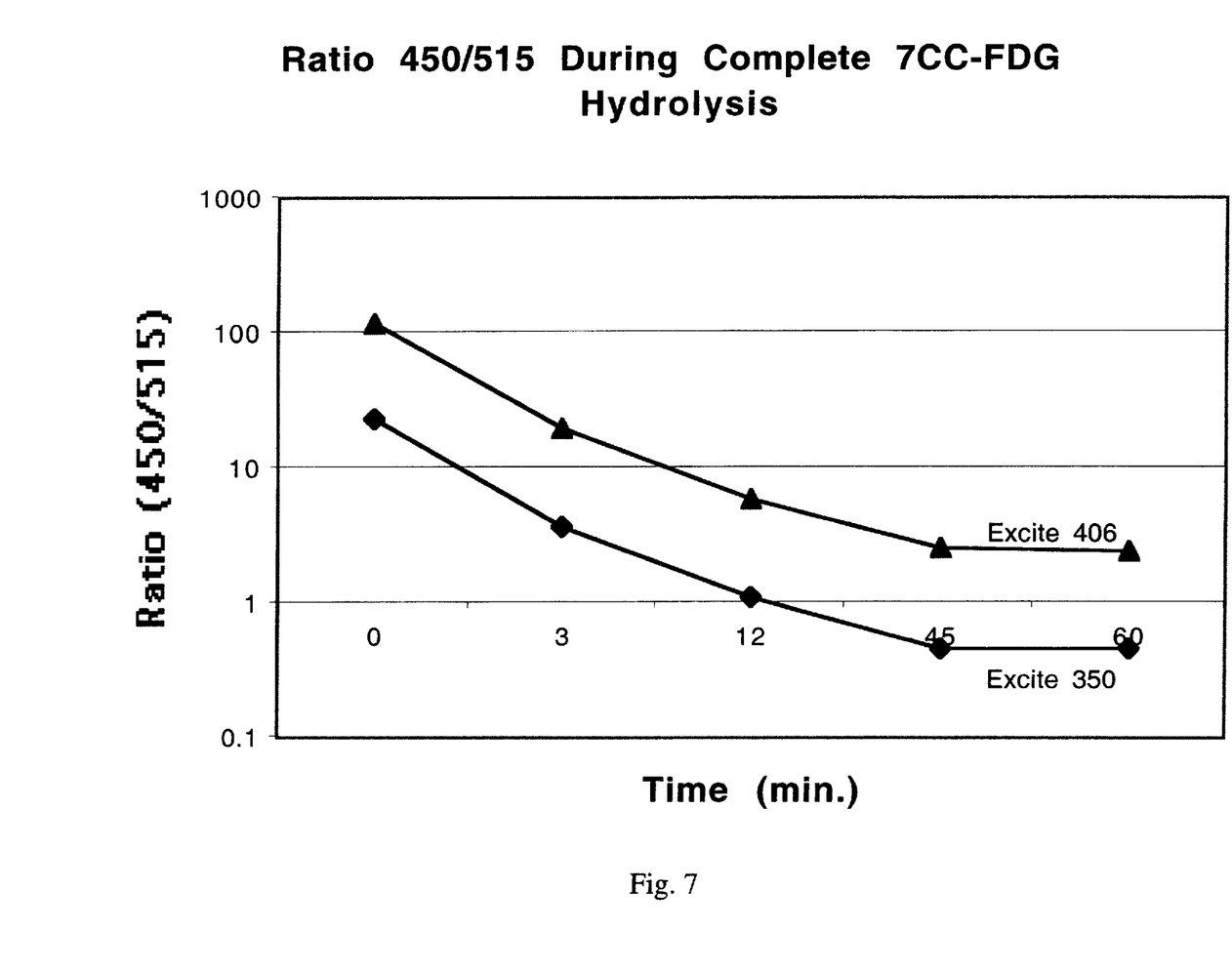
FIG. 7 is a graph showing the change in ratio of fluorescence of the compound at 450 nm and 515 nm as a function of time during hydrolysis with GUS, when excited at 350 nm and 406 nm.

A fluorimetery cuvette was prepared by adding 3 μL of 0.5 mM 7CC-FDG in DMSO (Compound F), to 3 mL of 50 mM Hepes buffer, pH 7.0, with 1 mM each $CaCl_2$ and $MgSO_4$. Fluorescent excitation and emission spectra of the sample were recorded using a Jobin-Yvon-SPEX Instruments Fluormax-2 fluorimeter under the following conditions: excitation at 300–500 nm with emission recorded at 515 or 530 nm (FIG. 4, scan A and B respectively); excitation at 350 nm and emission recorded at 425–650 nm (FIG. 4, scan C); excitation at 406 nm and emission recorded at 425–530 nm (FIG. 4, scan D); and excitation at 488 nm with emission recorded at 500–650 nm (FIG. 4, scan E). FIG. 5 shows the same set of scans performed 60 min. after the addition of 72 Units of β-glucuronidase (GUS, E. coli, purified, Sigma Chemicals, St. Louis, Mo.). FIG. 6 shows scans C, D and E taken before GUS addition and 3, 12, 45 and 60 min. after GUS addition. FIG. 7 shows the computed ratio as a function of time after GUS addition. The ratio computed is the emission at 450 nm when the exciting light was of 350 nm or 406 nm divided by the emission at 515 nm when the exciting light was of 488 nm.

These results show that the substrate can be cleaved by β-glucuronidase readily. The cleavage reveals a new fluorophore that is absent in the parent compound (compare scan E in FIG. 4 versus FIG. 5). The new fluorophore quenches the fluorescence of the coumarin moiety by more than 50% in the completely cleaved product (compare scan D, FIG. 6, at the 60 min. time point to the 0 min. time point). This quenching indicates that FRET occurred between the coumarin and fluorescein moieties. The compound exhibits a wide dynamic range, about 50 fold, measuring emission at 450/515 with excitation at 406 nm and 488 nm. This wide dynamic range provides for a robust assay. Because one of the most common laboratory lasers, the argon ion laser, emits at 350–360 nm in the long ultraviolet wavelengths, and also at 488 nm, the emission ratio at 450 nm/515 nm (excitation at 350 nm and 488 nm, respectively) was also computed (FIG. 7). This ratio also has a wide dynamic range; it varies by about 23 fold. This slightly lower range should also provide an adequate differential for a robust assay.

What is claimed:

1. A compound of the formula D—L—A*, wherein D comprises a fluorescent donor moiety capable of providing a fluorescent signal, and capable of acting as a donor moiety in a FRET signal; L comprises a linking group capable of maintaining D and A in a spatial relationship suitable for FRET, and A* comprises a pre-fluorescent moiety, comprising a fluorescent moiety capable of acting as a FRET acceptor coupled to a labile group that prevents A* from providing an effective signal.

2. The composition of claim 1, wherein said D—L—A* compound has the formula:

wherein $R_1$ is hydroxy, lower alkoxy, lower alkylamino, or di(lower alkyl)amino;

$R_2$ is H or halo;

$R_3$ and $R_4$ are each independently a sulfate, alkyl, acyl, acyloxymethyl, acyloxyethyl, choline, amino acid, oligopeptide, polypeptide, nucleotide, oligonucleotide, polynucleotide, carbohydrate, polysaccharide, lipid, or phospholipid group;

$X_1$ is H or OH;

$X_2$ is COOH, or $X_1$ and $X_2$ together form —COO—;

$X_3$ is a linking group; and $X_4$ and $X_5$ are each independently —O—, —NH—, —LO—, or —LNH—, where L is a cleavable linker.

3. The compound of claim 2, wherein $X_1$ and $X_2$ together form —C(=O)O—.

4. The compound of claim 2, wherein $X_3$ comprises a moiety of the form $L_1$—$L_2$—$L_3$, where $L_1$ is —$(CH_2)_n$NH, —$(CH_2)_n$CO, or —(CHR)CO, where R is lower alkyl and n is 0 to 6;

$L_3$ is CONH, $COCH_2S$, $(CH_2)_nR_{L3}$, $CH_2CO$, NHCO, $CH_2R_{L3}CH_2$, O, S, NH(CS)NH, where $R_{L3}$ is N, O, or S; and $L_2$ is an aliphatic, alicyclic, or heterocyclic moiety.

5. The compound of claim 4, where $L_2$ is selected from the group consisting of $L_{21}$, $L_{22}$, and $L_{23}$, where $L_{21}$ is —$A_1$—N(D)B—, where A is joined to $L_1$ and is $(CH_2)_n$, $NH(CH_2)_n$, $S(CH_2)_n$, or $O(CH_2)_n$, where n is 0–4, B is joined to $L_3$, and is $(CH_2)_m$, where m is 2–4, and D is $(CH_2)_m COOH$, $CH_2CH_2O(CH_2)_p COOH$ where p is 1–4;

$L_{22}$ is —$A_2$—E—, where $A_2$ is joined to $L_1$ and is selected from $(CH_2)_n$, $NH(CH_2)_n$, $S(CH_2)_n$, or $O(CH_2)_n$, where n is 0–4, and E is joined directly to $L_3$ and is C3–C7 alicyclic, phenyl or 6π heteroaryl, azaheterocyclic, oxaheterocyclic, substituted with at least one COOH and 0–4 groups selected from —$NO_2$, lower alkyl, and $CONH_2$; and $L_{23}$ is —$A_3$—$B_3$—$CH(RL_{L2})$—, where $A_3$ is joined to $L_1$ and is NH, O, or $CH_2$, $B_3$ is $CH_2$, CO, or CHOH, and $R_{L2}$ is H, $(CH_2)_n R_x$, or $CH_2O(CH_2)_n R_x$, where n is 0–4 and $R_x$ is lower alkyl, lower cycloalkyl, COOH, $CONH_2$, phenyl 0–4 groups selected from halo, OH, $OCH_2COOH$, $NH_2$, and $CH_2NH_2$.

6. The compound of claim 5, wherein E is selected from the group consisting of 6π heteroaryl, azaheterocyclic, oxaheterocyclic, substituted with at least one COOH and 0–4 groups selected from —$NO_2$, lower alkyl, and $CONH_2$, wherein said heteroaryl is selected from the group consisting of furan, thiophene, oxazole, thiazole, thiadiazole, and pyridyl, said azaheterocyclic is selected from the group consisting of azetidine, azetidinone, pyrrolidine, pyrrolidinone, piperidine, piperidinone, piperazine, oxazoline, and thiazoline, and said oxaheterocyclic is selected from the group consisting of tetrahydrofuran and tetrahydropyran.

7. The compound of claim 3, wherein $R_1$ is Cl, $R_2$ is OH, and $X_3$ is —CONH(CH$_2$)$_4$NH—COCH(CH$_2$CH$_2$COOH)NHCONH—.

8. The compound of claim 7, wherein $R_3$ and $R_4$ are each selected from the group consisting of carbohydrate and acyl.

9. The compound of claim 8, wherein $R_3$ and $R_4$ are each carbohydrate.

10. The compound of claim 8, wherein $R_3$ and $R_4$ are each acetyl.

11. The compound of claim 2, wherein $R_3$ and $R_4$ are each an oligopeptide.

12. A method for detecting an enzyme in a sample, comprising:
  a) providing a sample containing a detectable enzyme, or suspected of containing a detectable enzyme;
  b) contacting said sample with a compound of the formula D—L—A*, wherein D comprises a fluorescent donor moiety capable of providing a fluorescent signal, and capable of acting as a donor moiety in a FRET signal; L comprises a linking group capable of maintaining D and A in a spatial relationship suitable for FRET, and A* comprises a pre-fluorescent moiety, comprising a fluorescent moiety capable of acting as a FRET acceptor coupled to a labile group that prevents A* from providing an effective signal, wherein said labile group is cleavable by said enzyme;
  c) illuminating said sample with light having a frequency capable of stimulating fluorescence of said donor moiety; and
  d) detecting fluorescence generated by FRET from said acceptor moiety.

13. The method of claim 12, wherein said compound has the formula:

[chemical structure]

wherein
  $R_1$ is hydroxy, lower alkoxy, lower alkylamino, or di(lower alkyl)amino;
  $R_2$ is H or halo;
  $R_3$ and $R_4$ are each independently a sulfate, alkyl, acyl, acyloxymethyl, acyloxyethyl, choline, amino acid, oligopeptide, polypeptide, nucleotide, oligonucleotide, polynucleotide, carbohydrate, polysaccharide, lipid, or phospholipid group;
  $X_1$ is H or OH;
  $X_2$ is COOH, or $X_1$ and $X_2$ together form —COO—;
  $X_3$ is a linking group; and $X_4$ and $X_5$ are each independently —O—, —NH—, —LO—, or —LNH—, where L is a cleavable linker.

14. The method of claim 13, wherein $X_3$ comprises a moiety of the form $L_1$—$L_2$—$L_3$, where $L_1$ is —(CH$_2$)$_n$NH, —(CH$_2$)$_n$CO, or —(CHR)CO, where R is lower alkyl and n is 0 to 6;
  $L_3$ is CONH, COCH$_2$S, (CH$_2$)$_n$R$_{L3}$, CH$_2$CO, NHCO, CH$_2$R$_{L3}$CH$_2$, O, S, NH(CS)NH, where R$_{L3}$ is N, O, or S; and
  $L_2$ is an aliphatic, alicyclic, or heterocyclic moiety.

15. The compound of claim 14, where $L_2$ is selected from the group consisting of $L_{21}$, $L_{22}$, and $L_{23}$, where
  a) $L_{21}$ is —$A_1$—N(D)B—, where A is joined to $L_1$ and is (CH$_2$)$_n$, NH(CH$_2$)$_n$, S(CH$_2$)$_n$, or O(CH$_2$)$_n$, where n is 0–4, B is joined to $L_3$, and is (CH$_2$)$_m$, where m is 2–4, and D is (CH$_2$)$_m$COOH, CH$_2$CH$_2$O(CH$_2$)$_p$COOH where p is 1–4;
  b) $L_{22}$ is —$A_2$—E—, where $A_2$ is joined to $L_1$ and is selected from (CH$_2$)$_n$, NH(CH$_2$)$_n$, S(CH$_2$)$_n$, or O(CH$_2$)$_n$, where n is 0–4, and E is joined directly to $L_3$ and is C3–C7 alicyclic, phenyl or 6π heteroaryl, azaheterocyclic, oxaheterocyclic, substituted with at least one COOH and 0–4 groups selected from —NO$_2$, lower alkyl, and CONH$_2$; and
  c) $L_{23}$ is —$A_3$—$B_3$—CH(R$_{L2}$)—, where $A_3$ is joined to $L_1$, and is NH, O, or CH$_2$, $B_3$ is CH$_2$, CO, or CHOH, and $R_{L2}$ is H, (CH$_2$)$_n$R$_x$, or CH$_2$O(CH$_2$)$_n$R$_x$, where n is 0–4 and $R_x$ is lower alkyl, lower cycloalkyl, COOH, CONH$_2$, phenyl 0–4 groups selected from halo, OH, OCH$_2$COOH, NH$_2$, and CH$_2$NH$_2$.

16. A formulation comprising:
  a compound of the formula D—L—A*, wherein D comprises a fluorescent donor moiety capable of providing a fluorescent signal, and capable of acting as a donor moiety in a FRET signal; L comprises a linking group capable of maintaining D and A in a spatial relationship suitable for FRET, and A* comprises a pre-fluorescent moiety, comprising a fluorescent moiety capable of acting as a FRET acceptor coupled to a labile group that prevents A* from providing an effective signal; and
  a suitable carrier.

17. The formulation of claim 16, wherein said compound is a compound of the formula

[chemical structure]

wherein
  $R_1$ is hydroxy, lower alkoxy, lower alkylamino, or di(lower alkyl)amino;
  $R_2$ is H or halo;

$R_3$ and $R_4$ are each independently a sulfate, alkyl, acyl, acyloxymethyl, acyloxyethyl, choline, amino acid, oligopeptide, polypeptide, nucleotide, oligonucleotide, polynucleotide, carbohydrate, polysaccharide, lipid, or phospholipid group;

$X_1$ is H or OH;

$X_2$ is COOH, or $X_1$ and $X_2$ together form —COO—;

$X_3$ is a linking group; and $X_4$ and $X_5$ are each independently —O—, —NH—, —LO—, or —LNH—, where L is a cleavable linker.

* * * * *